United States Patent
Koniuk

(10) Patent No.: US 10,004,613 B1
(45) Date of Patent: Jun. 26, 2018

(54) LIMB SOCKET LINER SEALING SYSTEM

(71) Applicant: Wayne A. Koniuk, San Francisco, CA (US)

(72) Inventor: Wayne A. Koniuk, San Francisco, CA (US)

(*) Notice: Subject to any disclaimer, the term of this patent is extended or adjusted under 35 U.S.C. 154(b) by 0 days. days.

(21) Appl. No.: 15/297,289

(22) Filed: Oct. 19, 2016

Related U.S. Application Data

(63) Continuation-in-part of application No. 14/334,537, filed on Jul. 17, 2014.

(51) Int. Cl.
*A61F 2/80* (2006.01)
*A61F 2/78* (2006.01)

(52) U.S. Cl.
CPC .............. *A61F 2/80* (2013.01); *A61F 2/7812* (2013.01); *A61F 2002/802* (2013.01); *A61F 2002/805* (2013.01)

(58) Field of Classification Search
CPC ........ A61F 2/5044; A61F 2/5046; A61F 2/76; A61F 2/78; A61F 2/80; A61F 2002/802; A61F 2002/805; A61F 2002/807
See application file for complete search history.

(56) References Cited

U.S. PATENT DOCUMENTS

| | | | |
|---|---|---|---|
| 371,239 | A | 10/1887 | Winkley |
| 1,099,938 | A | 6/1914 | Rowley |
| 1,586,015 | A | 5/1926 | Underwood |
| 2,244,871 | A | 6/1941 | Guinzburg |
| 4,822,371 | A | 4/1989 | Jolly et al. |
| 4,908,037 | A | 3/1990 | Ross |
| 5,007,937 | A | 4/1991 | Fishman et al. |
| 5,376,131 | A | 12/1994 | Lenze et al. |
| 6,077,300 | A | 6/2000 | Sabolich et al. |
| 7,025,793 | B2 | 4/2006 | Egilsson |
| 7,144,429 | B2 | 12/2006 | Carstens |
| 7,169,188 | B2 | 1/2007 | Carstens |
| 7,351,264 | B2 | 4/2008 | Wilson |
| 7,655,049 | B2 | 2/2010 | Phillips |

(Continued)

FOREIGN PATENT DOCUMENTS

| | | |
|---|---|---|
| EP | 1875882 A | 1/2008 |
| WO | WO2013049847 A2 | 4/2013 |

OTHER PUBLICATIONS

Otto Bock. Caring for your prosthetic liner. Date verified Sep. 16, 2013 by the Wayback Machine.*

*Primary Examiner* — Thomas J Sweet
*Assistant Examiner* — Christie Bahena
(74) *Attorney, Agent, or Firm* — Goldstein Law Offices, P.C.

(57) ABSTRACT

A prosthetic limb attachment system, for attaching a residual limb segment having a distal end to a prosthetic limb having a socket having an open proximal end and a closed distal end, using a liner. The liner is made of a flexible material and has an open proximal end, a closed distal end, and liner walls extending therebetween. The liner has a sealing ring extending laterally inwardly from the walls that has a central opening. The liner is turned inside out and the liner walls are rolled up onto the residual limb segment so that the sealing ring may be positioned against the residual limb segment, oriented upwardly thereupon, to create a vacuum seal such that downward forces on the liner will only increase the vacuum seal with the residual limb segment.

7 Claims, 10 Drawing Sheets

(56) References Cited

U.S. PATENT DOCUMENTS

| | | | |
|---|---|---|---|
| 8,097,766 B2 | 1/2012 | Carlson et al. | |
| 8,114,167 B2 | 2/2012 | Caspers | |
| 8,409,299 B2 | 4/2013 | Kurth | |
| 2005/0267599 A1 | 12/2005 | Bjarnason | |
| 2007/0055383 A1 | 3/2007 | King | |
| 2008/0004717 A1* | 1/2008 | Asgeirsson | A61F 2/78 623/36 |
| 2008/0269914 A1 | 10/2008 | Coppens et al. | |
| 2009/0182435 A1 | 7/2009 | Haberman | |
| 2010/0004756 A1* | 1/2010 | Horie | A61F 2/7812 623/36 |
| 2010/0185300 A1* | 7/2010 | Mackenzie | A61F 2/7812 623/34 |
| 2011/0035027 A1 | 2/2011 | McCarthy | |
| 2011/0112656 A1* | 5/2011 | Kurth | A61F 2/80 623/33 |
| 2013/0035770 A1 | 2/2013 | Egilsson et al. | |
| 2013/0053982 A1 | 2/2013 | Halldorsson | |
| 2013/0131831 A1 | 5/2013 | Pianykh et al. | |
| 2013/0197670 A1 | 8/2013 | Mackenzie | |
| 2013/0289741 A1 | 10/2013 | Halldorsson et al. | |
| 2013/0331950 A1 | 12/2013 | Laghi et al. | |

* cited by examiner

LIMB SOCKET LINER SEALING SYSTEM

CROSS-REFERENCE TO RELATED APPLICATIONS

This application is a continuation-in-part of utility patent application Ser. No. 14/334,537 filed in the United States Patent Office on Jul. 17, 2014, claims priority therefrom, and is expressly incorporated herein by reference in its entirety.

TECHNICAL FIELD

The present disclosure relates generally to a limb socket liner for use in attaching a prosthetic limb socket to a residual limb segment. More particularly, the present disclosure relates to a system for providing a secure seal to the residual limb segment, so that the prosthetic limb may be comfortably worn for extended periods of time.

BACKGROUND

Conventional prosthetic limbs often have a socket for attaching onto the residual limb segment of the user. A liner is often employed between the socket and the residual limb segment to enhance the comfort of the user.

Generally these prosthetic devices rely on vacuum pressure for maintaining the prosthetic limb on the user. When the vacuum is broken, gravity will immediately pull the prosthetic off the user. When sweat forms, the friction is reduced and the air seal can be broken. In addition, when the muscles flex, or when a joint deflects, the liner can bunch up and form a channel for air to enter and break vacuum.

For below the knee amputations, the liner is long so that it encases the knee and extends way up into the thigh. Because it is held onto the residual limb segment by friction between the inside of the liner and the skin of the leg, it causes the amputee a great deal of discomfort. The possibility of skin breakdown is increased from bunching and pinching behind the knee as the knee is bent, and also from increased friction and pressure on the kneecap.

As a result, it would be highly desirable to cut the liner short, such that it does not cross over the knee or extend up the thigh. Doing so would clearly cut down on the restriction of knee bending and the discomfort associated with the present liners. However, using presently available technology, if the liner were cut down to the level of the socket, the prosthesis will fail. Clearly, what is needed in the art is a way to more securely attach the liner to the user, while eliminating the discomfort associated with presently available liner and prosthetic systems.

While the presently available systems and devices may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a liner that creates a vacuum seal with the residual limb segment of the user. Accordingly, the present disclosure providers a liner that includes a sealing ring that extends within the liner and extends upwardly therein to effectively retain the liner thereon, such that downward forces on the liner will only increase the vacuum connection between the liner and residual limb segment.

It is another aspect of an example embodiment in the present disclosure to provide a liner that provides enhanced comfort to the user, allows increased motion, yet does not sacrifice retention. Accordingly, with the effective vacuum seal created by the sealing ring, and the reduced reliance on friction between the residual limb and liner, the surface area of the liner can be greatly reduced, such that the liner can be shortened for below the knee amputation users, wherein anatomical cutouts may be provided to prevent interference with joint deflection and muscle movement.

It is yet another aspect of an example embodiment in the present disclosure to overcome the difficulty in providing an upwardly extending seal with the liner. Accordingly, the liner is made of a flexible material that allows the entire liner to be turned inside out. Thus, prior to donning the liner, it is turned inside out. The sealing ring is flipped toward the proximal end, and the walls of the liner are rolled up onto the residual limb segment to seat the sealing ring upwardly against the residual limb segment while the liner continues rolling upwardly beyond the sealing ring so that the liner walls hold the sealing ring in the upward position.

Accordingly, the present disclosure describes a prosthetic limb attachment system, for attaching a residual limb segment having a distal end to a prosthetic limb having a socket having an open proximal end and a closed distal end, using a liner. The liner is made of a flexible material and has an open proximal end, a closed distal end, and liner walls extending therebetween. The liner has a sealing ring extending laterally inwardly from the walls that has a central opening. The liner is turned inside out and the liner walls are rolled up onto the residual limb segment so that the sealing ring may be positioned against the residual limb segment, oriented upwardly thereupon, to create a vacuum seal such that downward forces on the liner will only increase the vacuum seal with the residual limb segment.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 3:
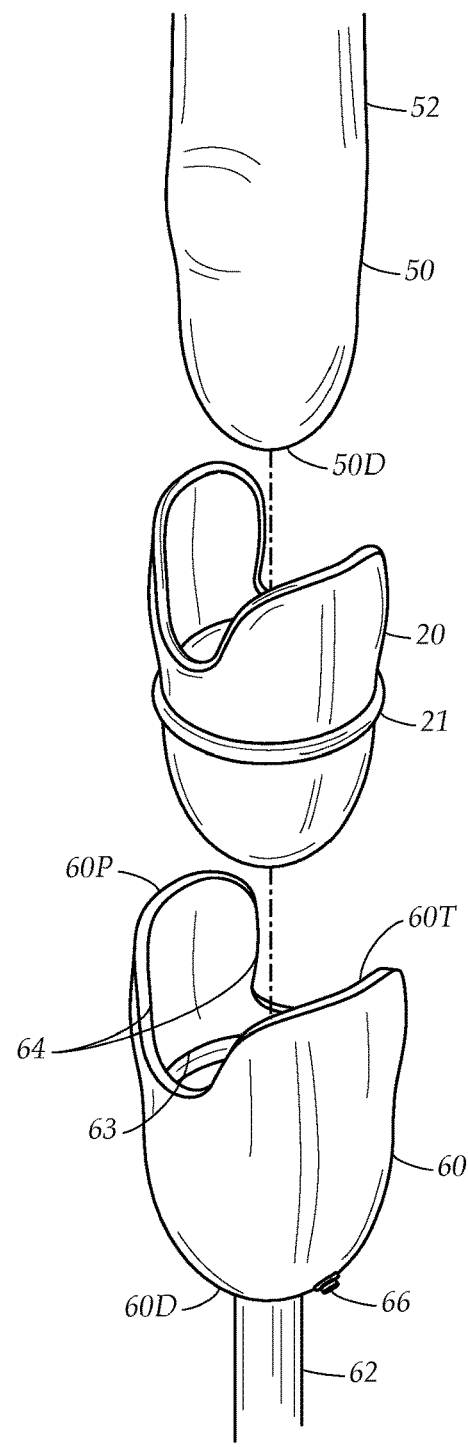
FIG. 3 is an exploded view, illustrating a residual limb segment being inserted into the liner, which in turn inserts into a prosthetic limb socket.

FIG. 3 illustrates a liner 20, for attachment onto a residual limb segment 50 of a user 52, for facilitating attachment of a prosthetic limb 62 that includes a socket 60. When worn by the user 52, the liner 20 allows the residual limb segment 50, having a distal end 50D, to be secured within the socket 60. As illustrated in FIG. 3, the socket 60 has an open proximal end 60P, and a closed distal end 60D. The socket 60 is a rigid shell that includes a top edge 60T at the proximal end 60P that includes anatomical adaptation cutouts 64 that facilitate attachment to the user 52 and allow suitable joint deflection and comfortable movement by the user 52. The socket 62 also has a vent 66 near the distal end 60D that facilitates venting air from the socket when inserting the liner 20, maintaining a vacuum seal within the socket 60 during use of the prosthetic limb 62, and breaking the vacuum seal for allowing removal of the liner 20 from the socket 60. To facilitate the vacuum seal between the socket 60 and liner 20, the liner 20 has an annular rib 21 that extends fully around the liner 20, and the socket 60 has a groove 63 that extends fully around its interior for accommodating the annular rib 21 and creating an airtight seal therewith to cause a vacuum chamber to occur between the annular rib 21 and the distal end 60D of the socket 60.

Figure 1:
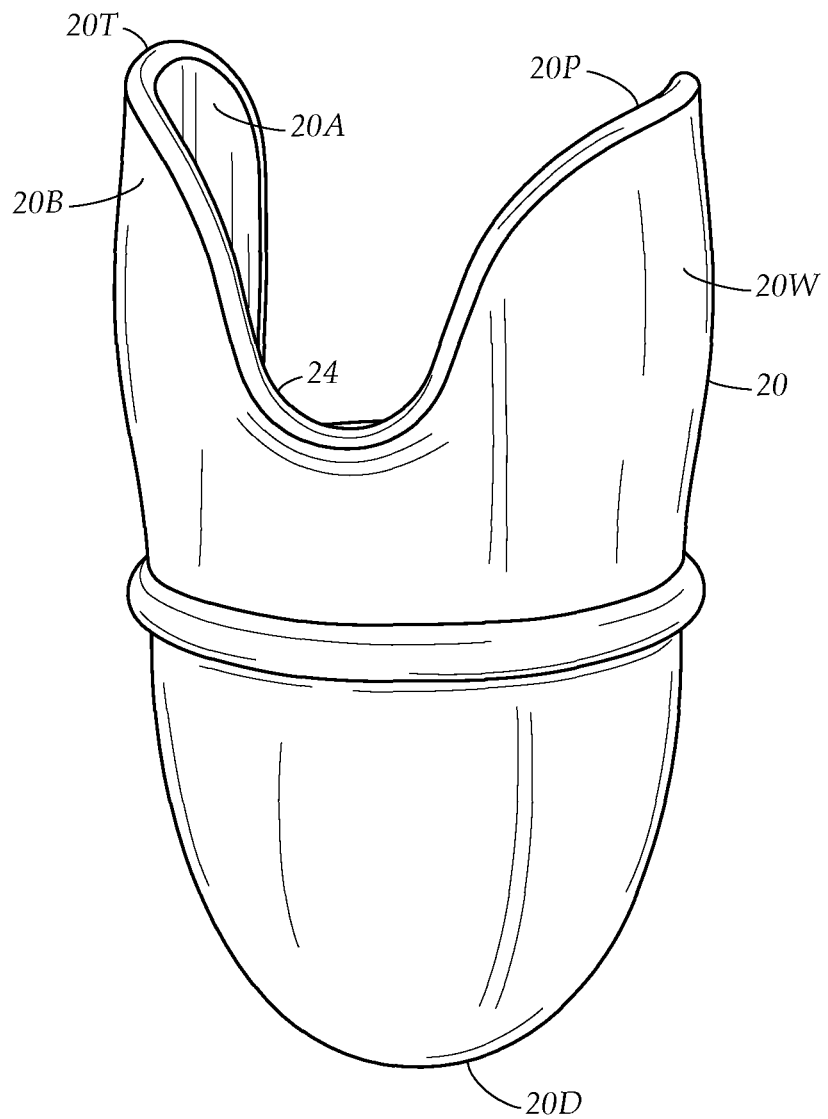
FIG. 1 is diagrammatic perspective view, illustrating a liner, in accordance with the present disclosure.
Figure 2:
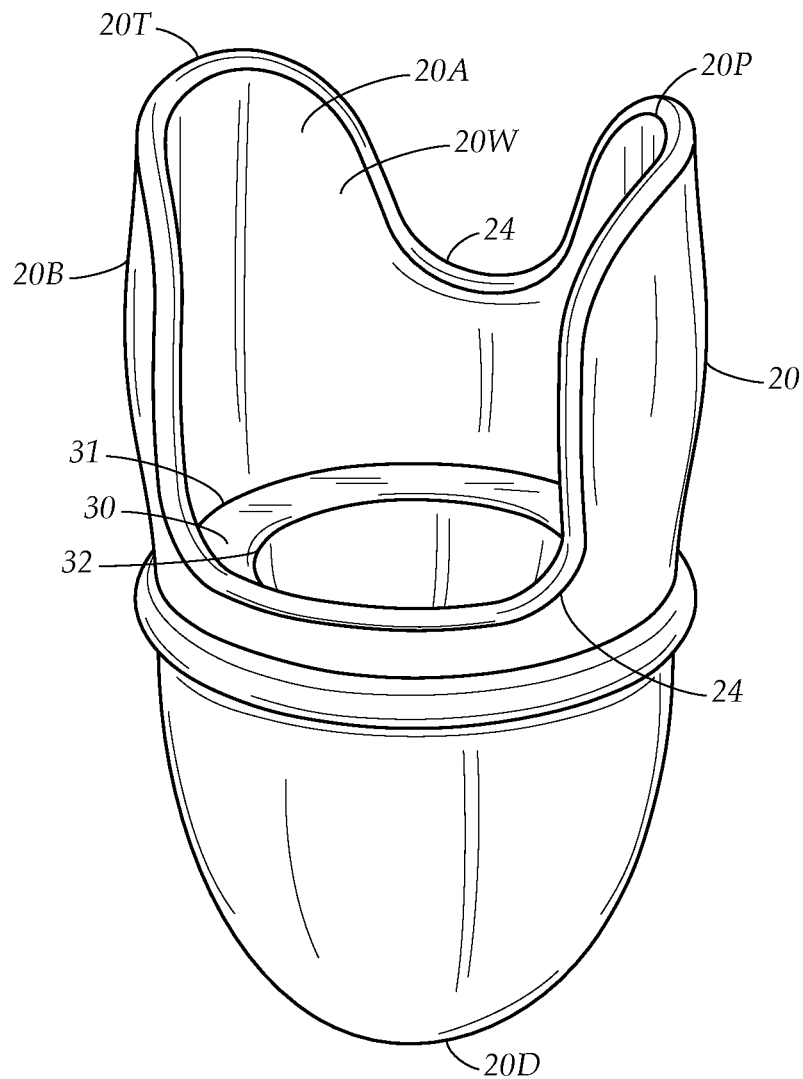
FIG. 2 is a diagrammatic perspective view, similar to FIG. 1, except wherein the liner has been axially rotated to show an internal sealing ring.

Referring to FIG. 1 and FIG. 2, the liner 20 has an open proximal end 20P and a closed distal end 20D. The liner 20 is fully flexible, made of an elastomeric, flexible material such as silicone, urethane, thermoplastic elastomer, a thermoplastic elastomer, or other material with rubber-like properties. Among these possibilities, silicone is the preferred material for the liner. The liner 20 has a top edge 20T and walls 20W that extend fully between the distal end and the top edge 20T, such that that liner 20 may be formed or cast of a single piece of material. The liner has an interior 20A and an exterior 20B. The top edge 20T has anatomical adaptation cutouts 24 that prevent interference with normal joint functioning, especially when used with a residual limb segment 20 of a below the knee or below the elbow amputation. Note that these cutouts 24 can be provided in the liner 20 according to the present disclosure due to its superior ability to create a vacuum seal as will be described hereinbelow, such that it does not need to rely on large surface area contact with the skin to stay put as in conventional liners.

Figure 5:
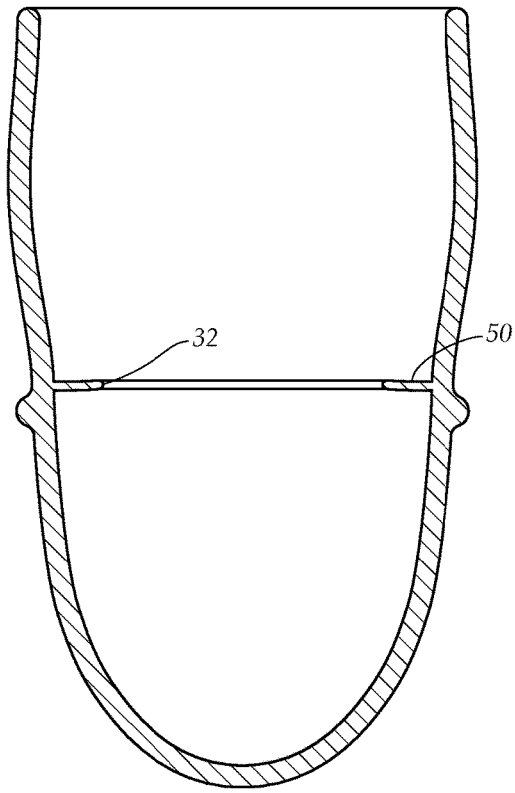
FIG. 5 is a front elevational view with parts broken away, illustrating just the liner in its natural, right-side out state, wherein the sealing ring extends inwardly within the walls of the liner.
Figure 5A:
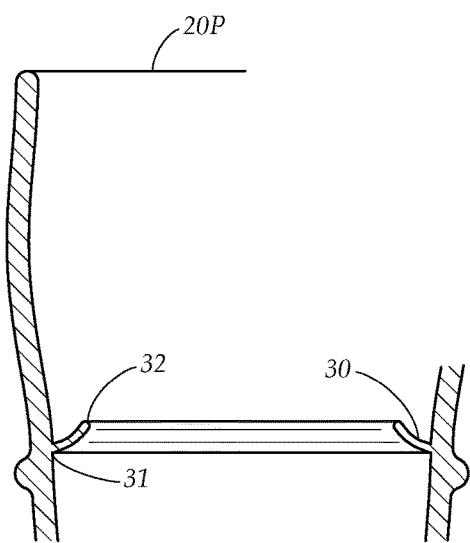
FIG. 5A is a front elevational view with parts broken away, similar to FIG. 5, except showing a further embodiment of the sealing ring, wherein the sealing ring extends concave upwardly.
Figure 6:
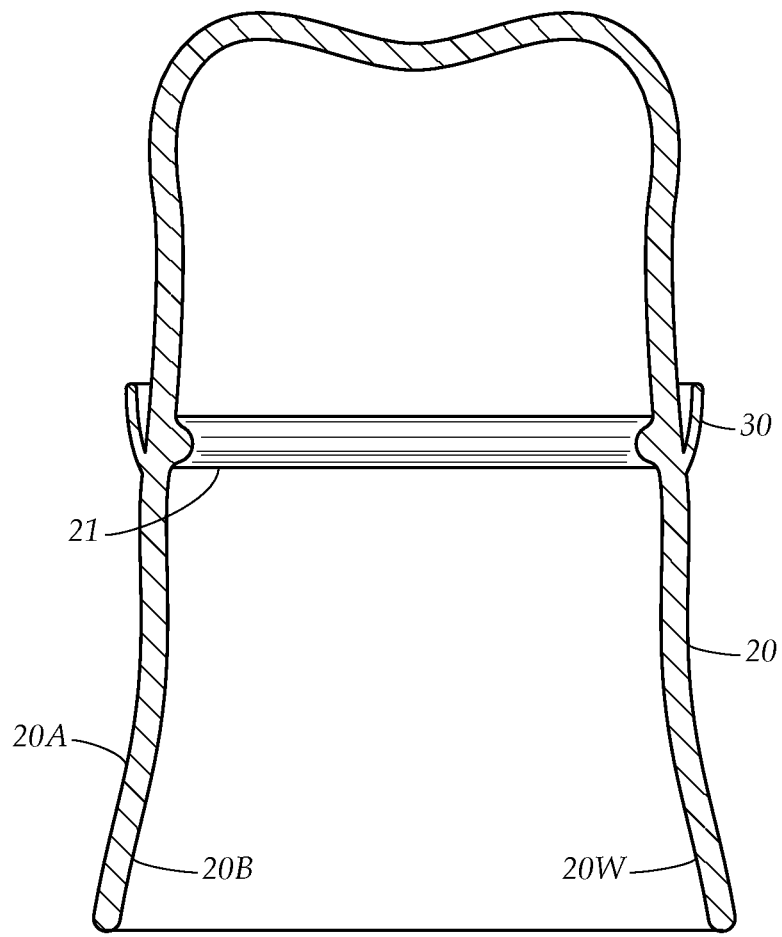
FIG. 6 is a front elevational view with parts broken away, illustrating the liner once it has been everted, wherein the sealing ring extends outwardly of the liner body and is extending toward the closed end.
Figure 7:
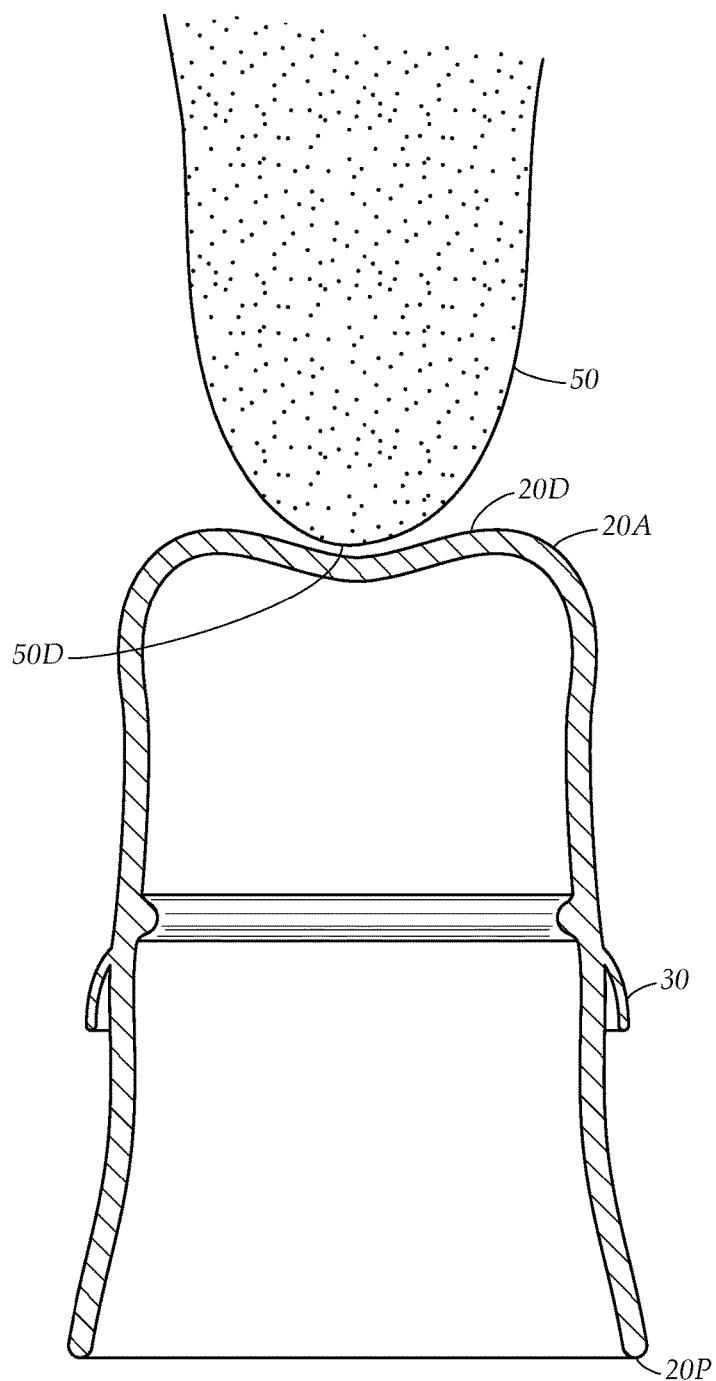
FIG. 7 is a front elevational view with parts broken away, showing the everted liner once the sealing ring has been flipped to extend toward the open end of the liner.

In accordance with the principles of the present disclosure, the liner includes a sealing ring 30 that extends inwardly from the walls 20W, and below the top edge 20T and any anatomical adaptation cutouts 24 thereof. The sealing ring 30 has an outer edge 31 where it meets the walls 20W and a central opening 32 that may flex and expand to accommodate the residual limb segment. Referring to FIG. 5, the sealing ring 30 may be provided as a simple diaphragm so that in its relaxed/unflexed state it extends neutrally inwardly within the liner 20 interior 20A, such that the outer edge 31 extends substantially perpendicularly inwardly from the walls 20W. In such embodiment, it sealing ring easily expands its central opening 32 to accommodate the residual limb segment extending therethrough and easily flexes upwardly to create a seal as described herein below. In addition, the sealing ring 20 may be provided with a natural upward concavity as seen in FIG. 5A, such that even when unflexed, the central opening 32 is further/closer toward the proximal end 20P than the outer edge 31.

Figure 4:
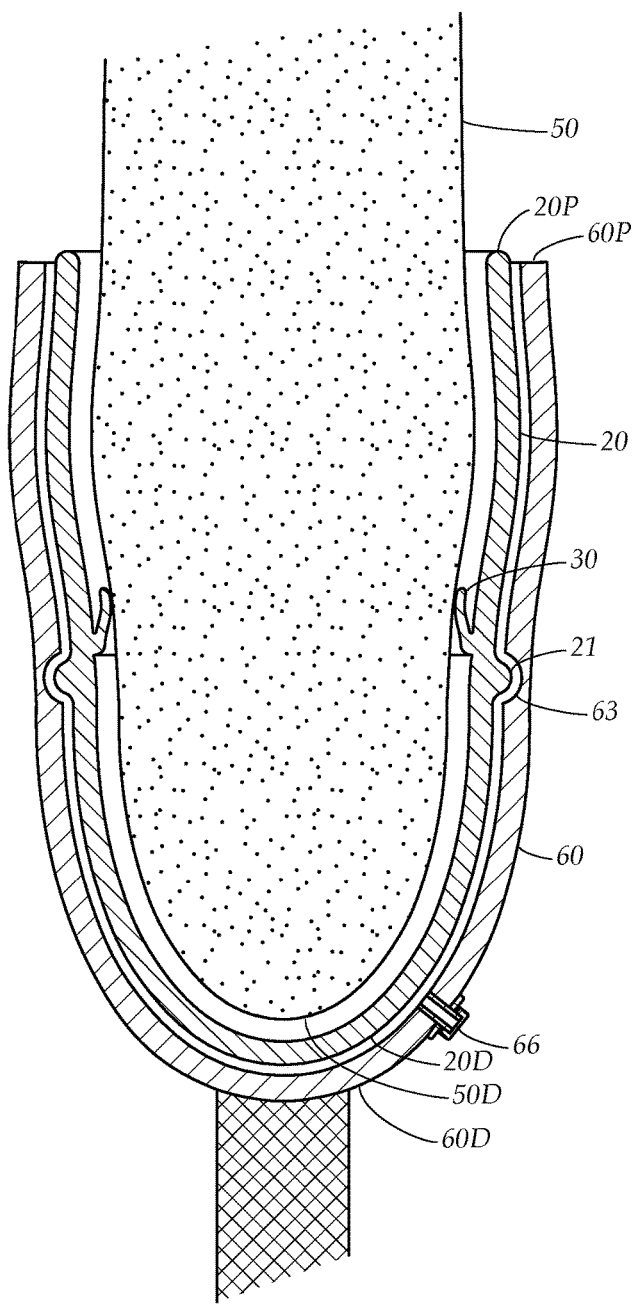
FIG. 4 is a front elevational view with parts broken away, illustrating the liner within the socket, and the residual limb segment within the liner, wherein the sealing ring extends upwardly against the residual limb segment to provide an airtight seal therebetween.

In order to create a vacuum seal between the residual limb segment 50 and the liner 20, the sealing ring 30 must be in the position shown in FIG. 4, where it extends upwardly on and against the residual limb segment 50, toward the proximal edge 20P of the liner 20. Note that "upwardly", as used herein, means away from the distal end 50D of the residual limb segment 50 and toward the torso of the user. "Downwardly", as used herein, means in a direction toward and beyond the distal end 50D, away from the torso of the user.

The liner 20 is tight fitting on the residual limb segment 50 by necessity. Clearly, any attempt to insert the residual limb segment 50 directly downwardly into liner 20 as shown would force the sealing ring 30 into a downward position, where it would not create the needed vacuum seal. Accordingly, achieving this upward positioning of the sealing ring 30 on the residual limb segment 50 is not possible using conventional apparatus and techniques in the field of prosthetics.

In accordance with the principles of the present disclosure, FIGS. 6-10 demonstrate critical steps in donning the liner 20 that allow the seal to be properly positioned to create the vacuum seal that is necessary for maintaining the liner 20 in position without relying on frictional contact between the liner 20 and skin. In particular, in FIG. 6, the liner 20 has been everted—that is, turned inside-out. Accordingly, the exterior 20B is not inside the walls 20W and the interior 20A is on the outside. The sealing ring 30 extends outwardly, and the annular rib 21 is located inside the liner 20. Note that according to its configuration, as the liner 20 is everted the sealing ring 30 may 'pop' to extend upwardly toward the distal end 20D. Note that the liner 20 is positioned with the distal end extending upwardly and the proximal end extending downwardly. Prior to application of the liner 20 to the user, the interior 20A and exterior 20B is coated with lubricating ointment, such as A&D OINTMENT, VASELINE, or the like. Next, referring to FIG. 7, the sealing ring 30 is flipped to extend downwardly toward the open proximal end 20P, and the distal end 20D of the interior 20A of the liner 20 is positioned against the distal end 50D of the residual limb segment 50 with the walls extending downwardly therefrom, away from the distal end 50D of the residual segment 50 with the open proximal end 20P of the liner 20 fully opposite from the distal segment 50D of the residual segment 50.

Figure 8:
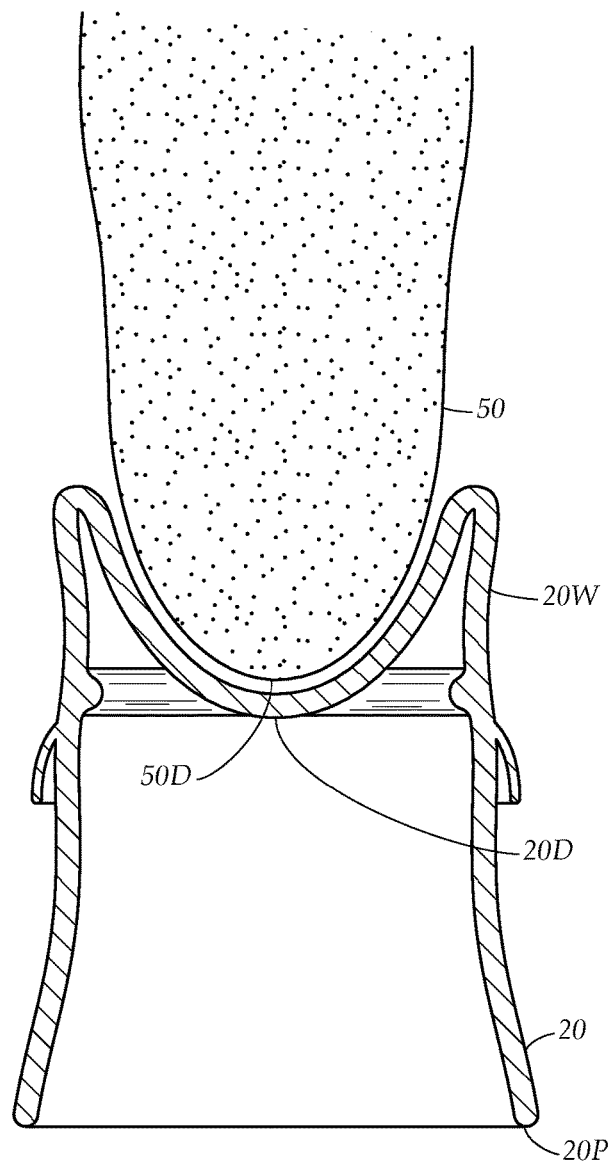
FIG. 8 is a front elevational view with parts broken away, wherein the distal end of the residual limb segment has been introduced centrally onto the bottom of the liner, and the liner bottom is moving downwardly to once again reform the liner interior, as the liner walls roll upwardly onto the residual limb segment.
Figure 9:
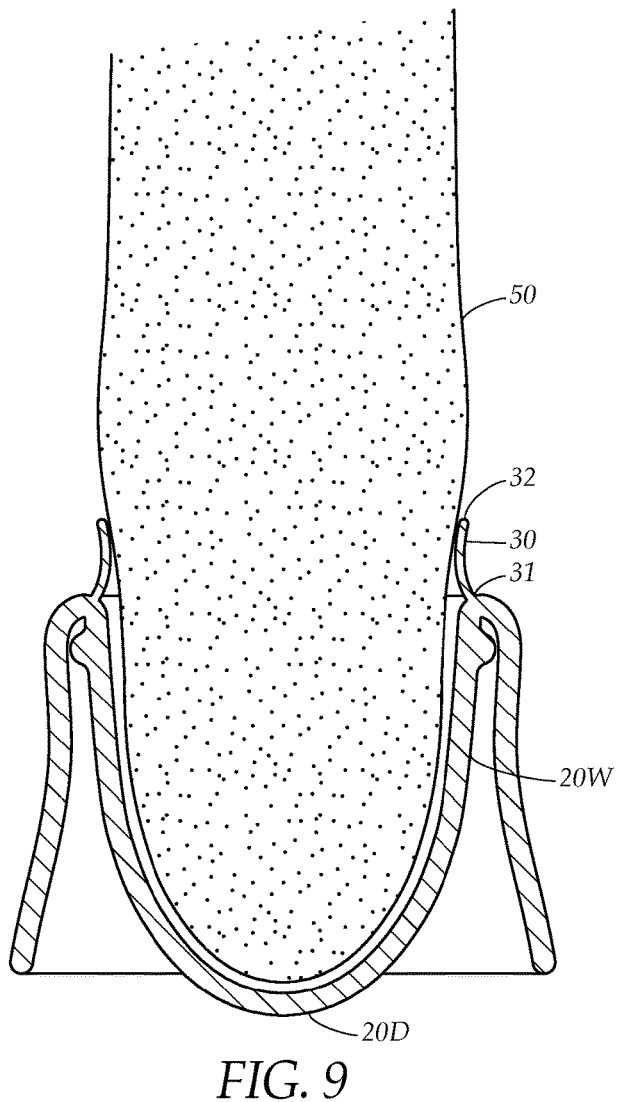
FIG. 9 is a front elevational view with parts broken away, wherein the liner has been rolled onto the residual limb segment to the height of the sealing ring, such that the sealing ring rests against the residual limb segment, extending upwardly and away from the distal end of the residual limb segment.
Figure 9A:
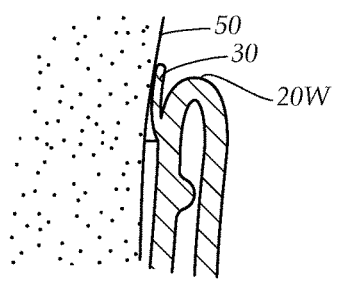
FIG. 9A is a front elevational view, with parts broken away, similar to FIG. 9, except depicting a moment immediately after the FIG. 9 wherein the wall has begun rolling upwardly over the sealing ring to hold the sealing ring against the residual limb segment.
Figure 10:
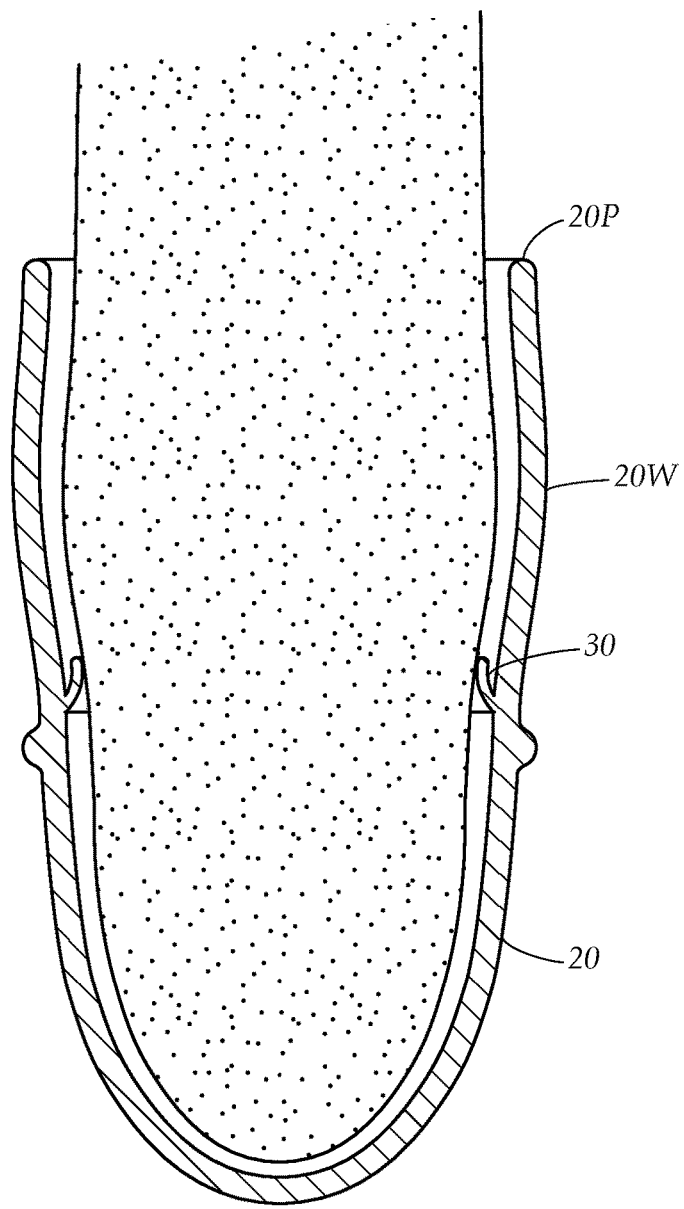
FIG. 10 is a front elevational view with parts broken away, wherein the liner has been fully rolled up onto the residual limb and is now again right-side out, wherein the seal extends upwardly toward the open end of the liner and away from the distal end of the residual limb segment.

Referring to FIG. 8, the walls 20W of the liner 20 are rolled upwardly from the distal end 20D of the liner 20 onto the residual limb segment 50, away from the distal end 50D of the residual limb segment, slowly turning the liner 'right side out' as the residual limb segment 50 is covered and engulfed within the liner 20, from its distal end 50D upwardly. Note, the sealing ring 30 still extends downwardly, and still toward the proximal end 20P. Referring to FIG. 9, as the walls 20W are rolled upwardly to where the outer edge 31 of the sealing ring 30 meets the walls 20W, the central opening 32 of the sealing ring 30 expands and contracts as the sealing ring 30 'swings up' to meet the residual limb segment 50, extending upwardly thereupon. And a moment later, as depicted in FIG. 9A, the walls 20W continue to roll up and hold the sealing ring 30 in that upward position against the residual limb segment 50. With the walls 20W holding it in place, the sealing ring 30 will remain oriented upwardly. As seen in FIG. 10, with the walls 20W fully rolled upwardly to the open proximal end 20P, the liner 20 is now fully right side out, the sealing ring 30 is in the position noted in the previous discussion of FIG. 4, and the liner is ready to insert into the socket 60. Again referring to FIG. 10, the sealing ring 30 effectively creates a vacuum seal that will keep the liner 20 on the residual limb 50 until it is desired to remove it. Downward force on the liner will only increase the vacuum effect that will thereby effectively resist any attempt or force acting to remove/move it downwardly, until the vacuum is broken, such as by manually stretching the liner outwardly with one's fingers.

Referring again to FIG. 4, with the residual limb segment 50 within the liner 20, the liner is then inserted into the socket 60, from the open proximal end 60P of the socket, downwardly until the distal end 20D of the liner 20 reaches the closed distal end 60D of the socket 60. The annual rib 21 engages the groove 63 to provide a vacuum seal between the liner 20 and the socket 50. Note that the distance/gap between the rib 21 and groove 63 has been exaggerated for illustration clarity, but in reality there is an interference fit between the rib 21 and groove 63. As the liner 20 is pressed into the socket 60, air is forced out through the vent 66, enhancing the vacuum seal between the liner 20 and socket 60.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a prosthetic limb attachment system that provides enhanced comfort to the user without sacrificing retention of the prosthetic device on the user. The disclosure is illustrated by example in the drawing figures, and throughout the written description. It should be understood that numerous variations are possible, while adhering to the inventive concept. Such variations are contemplated as being a part of the present disclosure.

What is claimed is:

1. A prosthetic limb attachment method, for attaching a residual limb segment having a distal end to a prosthetic limb having a socket having an open proximal end and a closed distal end, using a liner made of a one-piece flexible material having an open proximal end and a closed distal end and walls extending therebetween, the liner having a sealing ring extending laterally inwardly from the walls and having a central opening, comprising the steps of:
   turning the liner inside out;
   flipping the seal to extend downwardly toward the open proximal end of the liner;
   positioning the distal end of the liner against the distal end of the residual limb segment while the liner walls extend downwardly therefrom away from the distal end of the residual segment with the open proximal end of the liner fully opposite from the distal end of the residual limb segment; and
   creating a vacuum seal between the residual limb segment and liner while covering the residual limb segment with the liner by extending the sealing ring upwardly on the residual limb segment away from the distal end of the limb and toward the open proximal end of the liner, by turning the liner right-side out by rolling the liner upwardly onto the limb away from the distal end of the residual limb segment and;
   inserting the liner into the socket by inserting the distal end of the liner into the open proximal end of the socket and toward the distal end of the socket and the seal fully within the socket.

2. The prosthetic limb attachment method as recited in claim 1, wherein the step of positioning the distal end of the liner against the distal end of the residual limb segment is preceded by the step of coating the liner with lubricating ointment.

3. The prosthetic limb attachment method as recited in claim 2, wherein the liner is made from a material selected from the group consisting of Silicone, thermoplastic elastomer, and rubber.

4. A prosthetic limb attachment method, for attaching a residual limb segment having a distal end to a prosthetic limb having a socket having an open proximal end and a closed distal end, comprising the steps of:
   providing a liner made of a one-piece, flexible material having an open proximal end and a closed distal end and walls extending therebetween, the liner having a sealing ring extending laterally inwardly from the walls and having a central opening;
   turning the liner inside out;
   positioning the distal end of the liner against the distal end of the residual limb segment while the liner walls extend downwardly therefrom away from the distal end of the residual segment with the open proximal end of the liner fully opposite from the distal end of the residual limb segment;
   covering the residual limb segment with the liner and engaging the sealing ring with the residual limb segment by rolling the liner walls upwardly away from the distal end of the residual limb segment and against the residual limb segment; and
   inserting the liner into the socket by inserting the distal end of the liner into the open proximal end of the socket.

5. The prosthetic limb attachment method as recited in claim 4, wherein the step of engaging the sealing ring with the residual limb segment further comprises creating a vacuum seal between the residual leg segment and liner by extending the sealing ring between the liner walls and residual limb segment, upwardly on the residual limb segment away from the distal end of the residual limb segment and toward the proximal open end of the liner.

6. The prosthetic limb attachment method as recited in claim 5, wherein the liner is made entirely of silicone, and wherein the step of positioning the distal end of the liner against the distal end of the residual limb segment is preceded by the step of coating the liner with lubricating ointment.

7. The prosthetic limb attachment method as recited in claim 6, wherein the step of positioning the distal end of the liner against the distal end of the residual limb segment is preceded by the step of flipping the seal to extend downwardly toward the open proximal end of the liner.

* * * * *